United States Patent
Hong et al.

[11] Patent Number: 5,916,915
[45] Date of Patent: Jun. 29, 1999

[54] WATER-IN-STABLE L-ASCORBIC ACID DERIVATIVE AND A METHOD FOR PREPARATION THEREOF, AND A SKIN-WHITENING COSMETIC COMPOSITION CONTAINING THE SAME

[75] Inventors: Jong Eon Hong; Ki Hwa Lee; Jun Chul Cho, all of Seoul; Jang Sob Lee, Yongin; Jung No Lee, Kunpo; Ji Min Chun, Yongin; Dong Il Jang; Ok Sob Lee, both of Anyang; Sang Rhin Lee, Seoul, all of Rep. of Korea

[73] Assignee: Pacific Corporation, Seoul, Rep. of Korea

[21] Appl. No.: 09/090,226

[22] Filed: Jun. 4, 1998

[30] Foreign Application Priority Data

Jun. 4, 1997 [KR] Rep. of Korea .................. 97-23005
Mar. 17, 1998 [KR] Rep. of Korea .................. 98-9013

[51] Int. Cl.⁶ .................. A61K 31/34; C07D 307/26
[52] U.S. Cl. .................. 514/474; 514/844; 514/374; 549/315; 549/316; 549/335.1
[58] Field of Search .................. 514/474, 844, 514/374; 549/315, 316, 335.1

[56] References Cited

U.S. PATENT DOCUMENTS 5,723,645  3/1998  Lee et al. .................. 558/132

*Primary Examiner*—Johann Richter
*Assistant Examiner*—Taofiq A. Solola
*Attorney, Agent, or Firm*—Foley & Lardner

[57] ABSTRACT

Disclosed herein are a L-ascorbic acid derivative having an improved water-in-stability, represented by a following general formula (I):

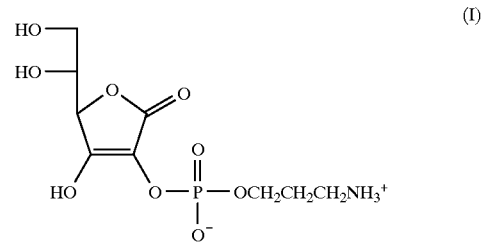

and a method for preparation thereof, and to a skin-whitening cosmetic composition containing the same as an active ingredient.

12 Claims, No Drawings

WATER-IN-STABLE L-ASCORBIC ACID DERIVATIVE AND A METHOD FOR PREPARATION THEREOF, AND A SKIN-WHITENING COSMETIC COMPOSITION CONTAINING THE SAME

BACKGROUND OF THE INVENTION

1. Field of the Invention

The present invention relates to a L-ascorbic acid derivative having an improved water-in-stability and a method for preparation thereof, and to a skin-whitening cosmetic composition containing the same as an active ingredient.

2. Related Arts

L-ascorbic acid has a strong anti-oxidation activity, promoting biosynthesis of collagen and proliferation of fibroblast. Especially, it is very effective in inhibiting melanin-formation and thereby can be employed in topical applications for purpose of preventing an abnormal pigmentation such as freckle.

However, ascorbic acid is easily decomposed by oxidation in an aqueous base to cause a reduction of activity during long-term storage.

Under this circumstance, the recent studies have been conducted to provide a new derivative which is stable in an aqueous base. The proposed derivatives are in the form of ester obtained by esterification of 2-, 3-, 5- or 6-position hydroxyl group of L-ascorbic acid with phosphoric or sulfuric group or fatty acid such as stearic acid and palmitic acid. The ester bond of these derivatives can be easily decomposed by a hydrolytic enzyme to release L-ascorbic acid and thereby provide effective physiological actions of L-ascorbic acid. For example, there is ascorbic acid 2-phosphate magnesium. This compound can be easily percutaneously penetrated by introduction of phosphoric group to deliver L-ascorbic acid to corium layer, as well as is itself very stable in an aqueous base without any discoloration by oxidation. So, this compound has been proposed as an active ingredient for skin-whitening cosmetic compositions (JP 1-283208A, JP 3-227907A).

However, although ascorbic acid 2-phosphate magnesium has some improvement in stability of itself, it has drawbacks in forming insoluble crystals by itself or precipitates with other ingredients such as anionic polymers and surfactants in an aqueous base. This precipitation is supposed to be due to low solubility in water.

Recently, ascorbic acid-2-O-α-glucoside has been proposed as a new material not having any above problem or drawback. This derivative is produced by fermentation. However, up to now, its percutaneous penetration or action for inhibiting melanin-formation are uncertain. In addition, it is very expensive because it is provided by fermentation.

Therefore, the present inventors have conducted extensive studies in order to provide a new derivative which itself is very stable and does not cause any precipitation in an aqueous base. They made efforts to find phosphoric group to be bonded to 2-hydroxyl group of L-ascorbic acid. As this phosphoric group, they considered 3-aminopropane phosphoric acid which has a good solubility in water to be employed in any type cosmetic compositions as far as they contain some water. That is to say, they introduced 3-aminopropane phosphoric acid into 2-hydroxyl group of L-ascorbic acid by phosphoric ester bond, to produce 2-(3-aminopropane phosphoric acid)-L-ascorbate.

Especially, 3-aminopropane phosphoric acid itself is active cosmetic material which can increase moisture retention ability, recuperation ability against the metamorphosis and firmness, of the skin, thereby deferring a skin aging effectively. In addition, it does not cause skin irritation and is stable to be easily formulated into the cosmetic products, as well as can promote cell-growth and biosynthesis of the epidermal collagen. Based on these effects and actions, cosmetic compositions containing 3-aminopropane phosphoric acid has been proposed in U.S. Pat. No. 5,723,645.

The present inventors confirmed that 2-(3-aminopropane phosphoric acid)-L-ascorbate itself is very stable without any discoloration and reduction of activity by oxidation and does not cause any precipitation in an aqueous base. Further, since this derivative can be easily percutaneously penetrated by phosphoric group, and once absorbed can be easily decomposed by a hydrolytic enzyme to release ascorbic acid and 3-aminopropane phosphoric acid, it is expected that a cosmetic composition containing this derivative can provide effective physiological actions onto the skin of both of L-ascorbic acid and 3-aminopropane phosphoric acid. Based on this expectation, the present invention has been completed.

SUMMARY OF THE INVENTION

Thus, an object of the present invention is to provide a new L-ascorbic acid derivative represented by a following general formula (I), which itself is very stable and does not cause any precipitation in an aqueous base:

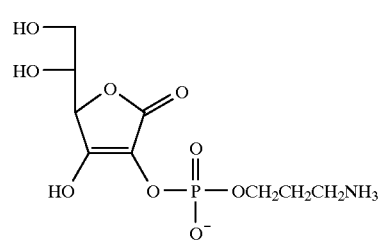

Further, another object of the present invention is to provide a method for preparing said L-ascorbic acid derivative (I), and to provide a skin-whitening cosmetic composition containing said L-ascorbic acid derivative (I) as an active ingredient, which can inhibit melanin-formation and thereby provide skin-whitening effect, as well as can prevent skin-wrinkling and thereby defer skin aging effectively.

DETAILED DESCRIPTION OF THE INVENTION

L-ascorbic acid derivative provided by the present invention is 2-(3-Aminopropane phosphoric acid)-L-ascorbate represented by a following general formula (I):

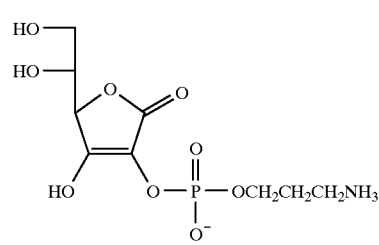

L-ascorbic acid derivative (I) (thereinafter, this compound will be referred to "AsA-APPA", which is an abbreviated name for ascorbic acid—aminopropanol phosphoric diester) is a compound where 3-aminopropane phosphoric acid is combined to 2-hydroxyl group of ascorbic acid by phosphoric ester bond. This compound is very stable without any discoloration and reduction of activity by oxidation in an aqueous base, and has a good solubility in water not to cause any precipitation. Further, it can be easily percutaneously penetrated by the phosphoric group, and once absorbed compound can be easily decomposed by a hydrolytic enzyme to release ascorbic acid and 3-aminopropane phosphoric acid. As a result, this compound can provide an activity for inhibiting melanin-formation by ascorbic acid and an activity for deferring skin-aging by 3-aminopropane phosphoric acid.

According to the present invention, the method for preparing AsA-APPA represented by the formula (I) partially comprises a method for preparing 3-aminopropane phosphoric acid(3-APPA) disclosed in U.S. Pat. No. 5,723,645. The disclosed preparation method of 3-APPA is simple and economic because it employs two-step process and inexpensive phosphorus oxychloride, thereby can be advantageously applied to an industrial scale.

In detail, the method for preparing L-ascorbic acid derivative (I) according to the present invention comprises steps of:

(1) reacting 3-amino-1-propanol with phosphorus oxychloride in an equivalent ratio of 1:1~1.3, in presence of an organic base, in an organic solvent, at a temperature of about 0~5° C. for about 1~2 hours, to produce 2-chlorotetrahydro-2H-1,3,2-oxazaphosphorin P-oxide represented by following general formula (II):

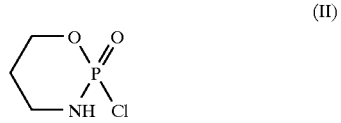

(II)

(2) reacting said compound (II) of said step (1) with 5,6-hydroxyl groups-protected L-ascorbic acid, in presence of an organic base, in an organic solvent, to produce L-ascorbic acid derivative represented by following general formula (III):

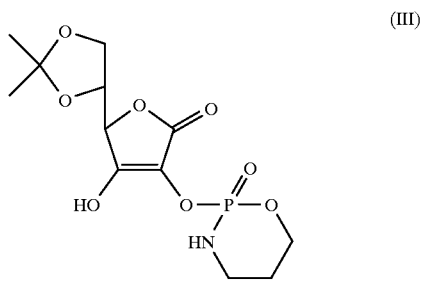

(III)

(3) hydrolyzing the L-ascorbic acid derivative (III) of said step (2) by adding distilled water thereto, at a temperature of about 5~100° C. for about 3 hours, to produce 2-(3-aminopropane phosphoric acid)-L-ascorbate;

(4) recrystallizing the product of said step (3) with a polar organic solvent; and (5) optionally neutralizing the product of said step (4) with an alkali or a base, to produce a salt.

The method may be represented by a following Reaction Scheme:

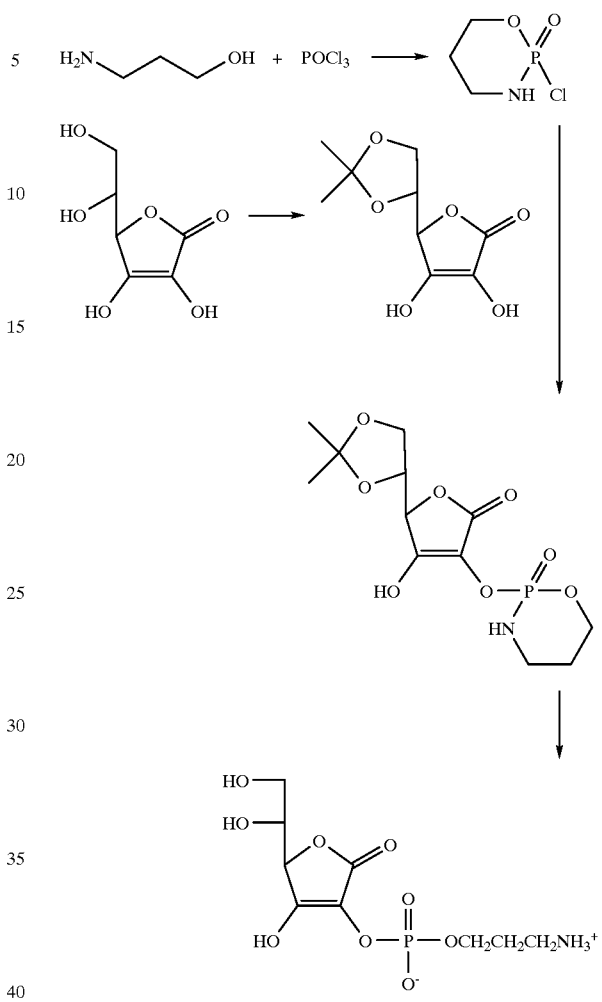

In the step (1), it is preferable that the reaction between 3-amino-1-propanol and phosphorous oxychloride is carried out in an equivalent ratio of 1:1~1.3. In case that this ratio is lower than 1:1, the objective product can not be obtained. While, in case that the ratio is higher than 1:1.3, excessive by-products as well as the objective product are obtained.

In this step, an intermediate 1:1 complex of 3-amino-1-propanol and phosphorous oxychloride is produced with a yield of 95% or more, and as a by-product 2:1 complex of 3-amino-1-propanol and phosphorous oxychloride is produced with a yield of 1~2% or less. However, the by-product may be removed by chromatography or crystallization with toluene. Specially, two of three chlorine atoms of phosphorous oxychloride are replaced by functional hydroxyl and amino groups of 3-amino-1-propanol, and cyclized to 2-chlorotetrahydro-2H-1,3,2-oxazaphosphorin P-oxide. And, the third chlorine atom is inactivated at a low temperature of 5° C. or less and is not replaced. The reason is that the chlorine atom of 2-chlorotetrahydro-2H-1,3,2-oxazaphosphorin P-oxide is stable in an inert anhydrous solvent and not replaced easily by 3-amino-1-propanol. Therefore, it is preferable to perform the reaction of the step (1) at a temperature of 5° C. or less, so as to prevent the production of the 2:1 by-product of 3-amino-1-propanol and phosphorous oxychloride. In this case, since the third chlorine atom of phosphorous oxychloride is not required to be protected by, for example ester groups or amide groups, the process can be carried out in a simple and easy way. While, since solubility of the reactant may be decreased and the reaction may proceed slowly and difficultly at a lower temperature than 0° C., amount of the unreacted materials may increase, resulting in a decrease of yield. Therefore, it is preferable to perform the reaction of the step (1) at a temperature of 0~5° C.

The organic base employed in this step may include, but not limited thereto, pyridine and triethylamine. Among them, triethylamine may be preferably employed.

Further, the organic solvent employed in this step may include, but not limited thereto, dichloromethane, tetrahydrofuran, ethyl acetate, acetonitrile, chloroform, ethyl ether and other inert solvents. Among them, dichloromethane may be preferably employed.

In the step (2), 5,6-hydroxyl groups of L-ascorbic acid may be masked by a protecting group such as benzylidene, phenylethylidene and isopropylidene. Among them, isopropylidene may be preferably employed as a protecting group.

The organic base employed in the step (2) may include, but not limited thereto, pyridine and triethylamine. Among them, triethylamine may be preferably employed.

Further, the organic solvent employed in the step (2) may include, but not limited thereto, dichloromethane, tetrahydrofuran, ethyl acetate, acetonitrile, chloroform, ethyl ether and other inert solvents. Among them, chloroform may be preferably employed.

The compound (III) produced in the step (2) is a strong acid in an aqueous solution (for example, pH2 in 1% of aqueous solution). So, the protecting group of 5,6-hydroxyl groups of the ascorbic moiety and the P—N bond of the oxazaphosphorin cyclic moiety can be easily hydrolyzed by adding distilled water without addition of acidic catalyst, thereafter by stirring at a temperature of 5~100° C., preferably of about 50° C., for about 3 hours.

The product can be purified by recrystallization with a polar organic solvent. The polar solvent may include, but not limited thereto, methanol, ethanol, isopropanol, acetone, tetrahydrofuran, acetonitrile or dioxane.

Further, the product, AsA-APPA may be preferably employed in a form of a salt obtained by neutralization with an alkali or a base, because the product is itself acidic. A neutralizing agent employed in this step (5) may include, but not limited thereto, alkali or metal oxides such as sodium carbonate, sodium hydroxide, potassium carbonate, potassium hydroxide, calcium hydroxide, magnesium hydroxide, calcium oxide and magnesium oxide; basic amino acids such as lysine, arginine and histidine; ammonia or amides such as triethanol amine; cationic polymers such as polyquaternium-4, -6, -7, -10, -11 and -16; and cationic surfactants such as lauryldimethylbenzyl ammonium chloride and stearyldimethylbenzyl ammonium chloride.

Further, the present invention can provide a skin-whitening cosmetic composition containing 2-(3-aminopropane phosphoric acid)-L-ascorbate or its salt produced by the above-described method as an active ingredient, which can inhibit melanin-formation and thereby provide skin-whitening effect, as well as can promote proliferation of fibroblast and thereby defer skin-aging effectively. The composition may contain 2-(3-aminopropane phosphoric acid)-L-ascorbate or its salt in an amount of 0.005~10% by weight, preferably 0.01~3% by weight, which can be chosen depending on the formulations or the final purposes of the composition. Further, the composition may be formulated, but not limited thereto, skin softner, astringents, nutrient toilet water, nutrient creams, massage creams, essences, eye creams, eye essences, cleansing creams, cleansing foams, cleansing water, packs, powders, body lotions, body creams, body oils or body essences.

PREFERRED EMBODIMENT OF THE INVENTION

The present invention will be described in more detail by way of the following examples. However, these examples are provided for only illustration purpose and should not be construed as limiting the scope of the invention, which is properly delineated in the accompanying claims.

PREPARATION EXAMPLE 1

Preparation of 2-chlorotetrahydro-2H-1,3,2-oxazaphosphorin P-oxide 34.1 ml(0.36 mol) of Phosphorous oxychloride was dissolved in 400 ml of dichloromethane. Then, the resulting solution was cooled to 0~5° C. in an ice bath.

In another reactor, 28 ml(0.36 mol) of 3-amino-1-propanol and 102 ml (0.73 mol) of triethylamine were diluted with 200 ml of dichloromethane and gradually added into the above solution for 2 hours. After the addition, the resulting mixture was filtered to remove triethylammonium chloride. The filtrate was washed with 100 ml of distilled water, and then dried over anhydrous sodium sulfate, filtered and concentrated under reduced pressure. Thereto was toluene added to give crystals. And then, the product was dried under reduced pressure to give 53 g of the title compound as white powder, which was identified by IR and NMR.

Melting Point: 79~82° C.

IR($CHCl_3$, $cm^{-1}$): 3254, 1477, 1274, 1092, 1036, 996

$^1$H-NMR($CDCl_3$): $\delta$(ppm)=1.7(m, 1H), 1.1(m, 1H), 3.3 (m, 2H), 4.4(m, 2H), 4.9(br, 1H)

$^{13}$C-NMR($CDCl_3$): $\delta$(ppm)=25.78, 25.85, 42.05, 42.11, 71.69, 71.81

PREPARATION EXAMPLE 2

Preparation of 2-(3-aminopropane phosphoric acid)-L-ascorbate 10 g(0.046 mol) of L-ascorbic acid with its 5,6-hydroxyl groups masked by isopropylidene was dissolved in 100 ml of chloroform, and then 12.9 ml(0.093 mol) of triethylamine was added thereto in an ice bath of 5° C. At the same temperature, 8.6 g(0.055 mol) of 2-chlorotetrahydro-2H-1, 3,2-oxazaphosphorin P-oxide produced in Preparation Ex. 1 was dissolved in 20 ml of chloroform and gradually added into the above solution. After the addition, the mixture was stirred at a room temperature overnight.

The organic layer was washed with an aqueous phosphoric solution, and then dried over anhydrous sodium sulfate and decolored with activated charcoal. The solution was filtered and concentrated under reduced pressure. Thereto was 30 ml of distilled water added, and stirred at a thermostat of 50° C. for 3 hours. Then, 150 ml of isopropanol was added to give crystals. And then, the product was dried under reduced pressure to give 6 g of the title compound as white powder, which was identified by IR and NMR.

Melting Point: 176~180° C.

IR(KBr, $cm^{-1}$): 3407, 3322, 3101, 2914, 1747, 1673, 1664, 1533, 1364, 1218, 1072

$^1$H-NMR($D_2O$): $\delta$(ppm)=1.9(m, 2H), 3.05(t, 2H), 3.62(m, 2H), 3.98(m, 3H), 4.90(s, 1H)

$^{13}$C-NMR($D_2O$): $\delta$(ppm)=26.76, 22.86, 32.35, 57.30, 59.77, 59.84, 64.15, 71.55, 71.72, 109.79, 109.88, 156.58, 156.63, 167.32, 167.38

PREPARATION EXAMPLES 3~7

Preparation of salts of 2-(3-aminopropane phosphoric acid)-L-ascorbate

In each example, 1 g of AsA-APPA produced in Preparation Ex. 2 was dissolved in 30 ml of distilled water, and then was added 5% of aqueous sodium carbonate solution in Preparation Ex. 3, 5% of aqueous potassium carbonate solution in Preparation Ex. 4, calcium hydroxide in Preparation Ex. 5, magnesium oxide in Preparation Ex. 6, and 5% of aqueous triethanolamine solution in Preparation Ex. 7, to make the solution pH7. The resulting solutions were freeze dried to give respective salts as white crystalline solids.

EXPERIMENTAL EXAMPLE 1 STABILITY OF AsA-APPA

L-Ascorbic acid and AsA-APPA produced in Preparation Ex. 2 were dissolved in buffer solutions of pH 7 to concentrations of 50 μM, respectively, and then maintained in a thermostat of 50° C. At constant intervals, UV absorbances were measured at 259 nm for AsA-APPA and at 266 nm for L-ascorbic acid, to evaluate the stabilities of the test samples as residual ratio(%). The results are shown in Table 1.

TABLE 1

|  | 30 min. | 1 hr. | 3 hr. | 6 hr. | 24 hr. | 6 days | 10 days |
|---|---|---|---|---|---|---|---|
| AsA-APPA | 100 | 100 | 100 | 100 | 99.1 | 95.5 | 93.5 |
| L-ascorbic acid | 17.2 | 1.0 | 0 | 0 | 0 | 0 | 0 |

As shown in the above Table 1, L-ascorbic acid was decomposed within about 1 hour, while AsA-APPA of the present invention was very stable in the neutral aqueous solution.

EXPERIMENTAL EXAMPLE 2 STABILITY OF AsA-APPA IN AN AQUEOUS BASE

Each 3 g of compounds of Preparation Ex. 3 and Ex. 6 and L-ascorbic acid 2-phosphate magnesium was dissolved in 100 ml of distilled water, and then maintained in a thermostat of 50° C. for 30 minutes. Precipitation and discoloration were observed with the lapse of time. The results are shown in Table 2.

TABLE 2

| Lapsed days | | 1 | 3 | 5 | 7 | 9 | 11 | 13 | 15 | 30 |
|---|---|---|---|---|---|---|---|---|---|---|
| Prep. Ex. 3 | Precipitation | – | – | – | – | – | – | – | – | – |
|  | Discoloration | – | – | – | – | – | – | – | – | – |
| Prep. Ex. 6 | Precipitation | – | – | – | – | – | – | – | – | – |
|  | Discoloration | – | – | – | – | – | – | – | – | – |
| Comp. Ex. 1 | Precipitation | – | + | + | ++ | ++ | ++ | +++ | +++ | +++ |
|  | Discoloration | – | – | – | – | – | – | – | – | + |

(Note)
| Evaluation System | Precipitation | Discoloration |
|---|---|---|
| – | No precipitation | Colorless or pale-yellow |
| + | Slight precipitation | A little discoloration |
| ++ | Some precipitation | Severe discoloration |
| +++ | Severe precipitation | Extremely severe discoloration |

As shown in the above Table 2, the compounds of the present invention did not cause precipitation in the aqueous base and discoloration with the lapse of time.

EXPERIMENTAL EXAMPLE 3 PROLIFERATION OF FIBROBLAST

The skin obtained from new epidermal tissue was treated with Type 1 collagenase to remove epidermis. The obtained fibroblast was cultured on Dulbecco's Modified Eagle's Media(DMEM).

Amount of fibroblast was measured by way of MTT method. The result was that the compound of Preparation Ex. 2 shows an effective fibroblast proliferation at a concentration as low as 10 mM.

EXPERIMENTAL EXAMPLE 4 SAFETY OF AsA-APPA TO THE LIVING BODY

Because cosmetic materials are applied onto the skin, their safety in the living body is very important. In the present invention, toxicity and irritation of AsA-APPA to the body were examined through the following experiments. The results proved that AsA-APPA was safe to the living body.

(4-1) Acute Oral Toxicity Test 10 ml/kg of AsA-APPA of Preparation Ex. 2 was diluted with physiological saline to give 50% of test sample. This test sample was orally administrated into the ten(10) of ICR mice(five males and five females) weighing 20~33 g (administrated amount of AsA-APPA: 5 g/kgweight). As a control, 10 ml/kg of physiological saline was orally administrated into the ten(10) of ICR mice(five males and five females) weighing 20~33 g (administrated amount of AsA-APPA: 0 g/kgweight).

At that day, general appearance was observed every hour for 6 hours. And, from the next day to 14 days, every day, were observed general appearance(clinical symptoms), toxic symptoms, death and the like. Further, change of weight was measured at 1, 3, 7 and 14 days.

Any of the mice dead during observation period were immediately subjected to autopsy, and the survival mice were subjected to autopsy after observation period. Internal organs were observed with naked eyes and in case of abnormal symptoms, subjected to pathologic histotest.

As a result, there was no dead mice and, no significant difference was observed in the weight changes in comparison to the control. And, autopsy protocol said that no abnormal symptom was observed.

And, according to the Litchfield-Wilcoxon's method, $LD_{50}$(lethal dose) of AsA-APPA is 5 g/kg in the acute oral exposure.

(4-2) Acute Dermal Toxicity Test 4 ml/kg of AsA-APPA of Preparation Ex. 2 was diluted with physiological saline to give 50% of test sample. This test sample was percutaneously administrated into the ten (10) of ICR mice(five males and five females) weighing 20~33 g (administrated amount of AsA-APPA: 2 g/kgweight). As a control, 4 ml/kg of physiological saline was percutaneously administrated into the ten(10) of ICR mice(five males and five females) weighing 20~33 g (administrated amount of AsA-APPA: 0 g/kgweight).

Before about 24 hours, the back of each mouce was depilated in a size of 1.5×1.5 $cm^2$. Then, each depilated site was covered with a gauze of 1×1 $cm^2$ applied with one of the test and control samples, and fixed using an non-irritative tape, for 24 hours.

At that day, general appearance was observed every hour for 6 hours. And, from the next day to 14 days, every day, were observed general appearance(clinical symptoms), toxic symptoms, death and the like. Further, change of weights was measured at 1, 3, 7 and 14 days.

Any of the mice dead during observation period were immediately subjected to autopsy, and the survival mice were subjected to autopsy after observation period. Internal organs were observed with naked eyes and in case of abnormal symptoms, subjected to pathologic histotest.

As a result, there was no dead mice and, no significant difference was observed in the weight changes in comparison to the control. And, autopsy protocol said that no abnormal symptom was observed.

And, according to the Litchfield-Wilcoxon's method, $LD_{50}$(lethal dose) of AsA-APPA is 2 g/kg in the acute dermal exposure.

(4-3) Primary Skin Irritation Test

Test was carried out for twelve(12) of New Zealand White male rabbits whose backs were depilated before 24 hours. And, 0.1 ml of AsA-APPA of Preparation Ex. 2 was diluted with physiological saline to give 50% of test sample.

The test sample was applied to two sites (2.5 cm×2.5 cm) of the right back (amount of AsA-APPA per site: 0.5 ml). As a control, two sites (2.5 cm×2.5 cm) of the left back were treated with 1.0 ml of physiological saline. Each tested site was covered with a gauze, which was fixed using an non-irritative tape. 24 Hours later, the tested sites were washed with physiological saline.

As a result, no skin abnormality such as erythema and edema was observed for 24 or 72 hours after removing the patches. And, the Draize's PII(Primary Irritation Index) due to erythema is 0.13, indicating that AsA-APPA is non-irritative or very low-irritative, it any.

(4-4) Eye Irritation Test

Test was carried out using the nine(9) of New Zealand White rabbits.

0.1 ml of AsA-APPA of Preparation Ex. 2 was diluted with physiological saline to give 10% of test sample. This test sample was dropped onto the right eye of each rabbit, taking the left eye as a control. After 20~30 seconds, only three(3) rabbits of them were washed sufficiently with the sterilized saline.

After 24 hours or 48 hours, no eye irritation on cornea, iris and conjunctiva was observed. Irritation rate of eye mucos (M.O.I) was 0.0 in both washed and non-washed cases.

(4-5) Skin Sensitization Test

Test was carried out for six(6)(three males and three females) of Guinea pigs(Hartley Albino Guinea Pig) weighing 300~360 g according to Maggnusson and Kligman's procedure (Guinea Pig Maximization test).

In order to determine the concentrations of the test samples to be applied in Induction test for light irritation and Challenge test for no irritation, for three(3) of Guinea pigs for each test, primary irritations were taken with 6.25%, 12.5% and 25.0% of the test samples, respectively. For each animal, each site (2.5×2.5 cm) of right and left of the back was treated with three concentrations of the test samples in an amount of 0.5 ml/site of AsA-APPA, and then covered with a gauze, which was fixed using an non-irritative tape, for 24 hours. Next, 0.1 ml of 25% of AsA-APPA was intradermally injected to each of two pigs(one male and one female) using 26-gauge ½-inched needle. 7 Days later, the same sites were depilated and pretreated with 10% of SLS in petrolatum. Then, each tested site was treated with 0.5 ml/site of AsA-APPA, and then covered with a gauze, which was fixed using an non-irritative tape, for 48 hours. 2 Weeks later, the left back of the depilated pig was treated with the test sample and the right back was treated with physiological saline. 24 Hours later, the tested sites were washed with physiological saline.

As a control, test was carried out using physiological saline, instead of the test sample, in the same procedure.

As a result, no skin abnormality such as erythema and edema was observed for 24, 48 and 72 hours after removing the patches. And, according to the Kligman's criterion, 1 grade was given to AsA-APPA, indicating that AsA-APPA is very safe to the skin.

(4-6) Human Patch Test

Test was carried out for thirty(30) of healthy females aging 20~30 years according to CTFA Guideline(The Cosmetic, Toiletry and Fragrance Association. Inc. Washington, D.C., 20023, 1991).

The back of the subjected was washed with 70% of ethanol and dried, and then, applied with a finn chamber containing 20 μl of patch base incorporating 10% of AsA-APPA of Preparation Ex. 2. The finn chamber was fixed to the tested site using a micropore tape. 24 hours later, the tape and the chamber were removed, and the tested site was marked with marking pen. After 24 hours or 48 hours, skin responses of the tested sites were observed and skin irritation were evaluated according to ICDRG(International Contact Dermatitis Research Group)'s criterion.

As a result, primary irritative response, except for 1% of erythema, was hardly observed, but after 48 hours, all the irritation fade away. Average response was 0.42.

TABLE 3

| Sample | Response (%), N = 30 | | |
| --- | --- | --- | --- |
| | 24 hr. | 48 hr. | Average Response* |
| AsA-APPA | 1 | 0 | 0.42 |
| Patch base | 1 | 0 | 0.42 |

*Average Response = Grade of the sample/4(Maximum grade) × 30(Total sample) × 100 × ½

(4-7) Repeat Insult Human Patch Test

Test was carried out for twenty(20) of healthy females aging 20~30 years according to CTFA Guideline(The Cosmetic, Toiletry and Fragrance Association. Inc. Washington, D.C., 20023, 1991).

The back of the subjected was washed with 70% of propanol and dried, and then, applied with a finn chamber containing 20 μl of patch base incorporating 10% of AsA-APPA of Preparation Ex. 2. Applications were repeated every 24 hours for 3 weeks (Induction Period). After about 2 weeks, Challenge Insult Patch was carried out. At this step, the sites tested during the induction period and new sites were applied with the patches for 48 hours. Later, the patches were removed, and skin responses of the tested sites were observed at 24, 48 and 72 hours thereafter. And, skin irritation was evaluated according to ICDRG(International Contact Dermatitis Research Group)'s criterion.

As a result, no repeat irritation or no sensitive irritation was observed. Average response was 0.14 and 0 during the induction period and during the challenge period, respectively.

TABLE 4

| | Induction Period (weeks) | | | Average Response (%) | Challenge Period (hours) | | | Average Response (%) |
| --- | --- | --- | --- | --- | --- | --- | --- | --- |
| Sample | 1 | 2 | 3 | n = 20 | 24 | 48 | 72 | n = 20 |
| AsA-APPA | 1 | — | — | 0.14 | — | — | — | 0 |
| Patch base | — | 1 | — | 0.14 | — | — | — | 0 |

The results of the Tests (4-1) to (4-7) were summarized in Table 5.

TABLE 5

| Items | Results | Evaluation |
|---|---|---|
| Acute oral toxicity test | $LD_{50} > 5$ g/kg | Innoxious |
| Acute dermal toxicity test | $LD_{50} > 2$ g/kg | Innoxious |
| Primary skin irritation test | PII = 0.13 | Little irritative |
| Eye irritation test | M.O.I. = 0 | No irritative |
| Skin sensitization test | Kligman's grade: 1 | Slightly sensitive |
| Human patch test | Average Response = 0.42 | No irritative |
| Repeat insult human patch test | Average Response = 0.14 | No irritative |

Through the above experiments, it is proved that AsA-APPA is a safe material for topical applications on the skin.

EXAMPLE 1 AND COMPARATIVE EXAMPLES 1~5 CREAMS

EXPERIMENTAL EXAMPLE 5 SAFETY TO THE SKIN

In order to evaluate safety of whitening cosmetic compositions containing AsA-APPA onto the skin, the conventional patch test was carried out for compositions of Examples 1~2 and Comparative Examples 1~10, and the level of skin irritation was estimated according to the following scoring system:

<Evaluation System>

+++ Extremely severe irritation, estimated to be inadequate as a cosmetic
++ Severe irritation, estimated to be better not to use as a cosmetic
+ A little irritation, estimated to be carefully used as a cosmetic
± Little irritation

|  | Example | Comparative Examples | | | | |
|---|---|---|---|---|---|---|
| Materials | 1 | 1 | 2 | 3 | 4 | 5 |
| Cetostearyl alcohol | 1.0 | 1.0 | 1.0 | 1.0 | 1.0 | 1.0 |
| Lipophilic monostearic glycerine | 1.0 | 1.0 | 1.0 | 1.0 | 1.0 | 1.0 |
| Monostearic polyoxyethylene sorbitan(EO = 20) | 1.5 | 1.5 | 1.5 | 1.5 | 1.5 | 1.5 |
| Self-emulsified monostearic glycerine | 1.0 | 1.0 | 1.0 | 1.0 | 1.0 | 1.0 |
| Caprylic/capric triglyceride | 6.0 | 6.0 | 6.0 | 6.0 | 6.0 | 6.0 |
| Liquid paraffin | 7.0 | 7.0 | 7.0 | 7.0 | 7.0 | 7.0 |
| Squalane | 3.0 | 3.0 | 3.0 | 3.0 | 3.0 | 3.0 |
| Tocopheryl acetate | 1.0 | 1.0 | 1.0 | 1.0 | 1.0 | 1.0 |
| Alantoin | 0.3 | 0.3 | 0.3 | 0.3 | 0.3 | 0.3 |
| Glycerine | 7.0 | 7.0 | 7.0 | 7.0 | 7.0 | 7.0 |
| Propylene glycol | 7.0 | 7.0 | 7.0 | 7.0 | 7.0 | 7.0 |
| Xantan gum | 0.5 | 0.5 | 0.5 | 0.5 | 0.5 | 0.5 |
| Preservative | q.s. | q.s. | q.s. | q.s. | q.s. | q.s. |
| Perfume | q.s. | q.s. | q.s. | q.s. | q.s. | q.s. |
| L-ascorbic acid(AsA) | — | — | 0.5 | — | — | 0.25 |
| 3-Aminopropane phosphoric acid(3-APPA) | — | — | — | 0.5 | — | 0.25 |
| AsA-APPA(Prep. Ex. 3) | 0.5 | — | — | — | — | — |
| L-ascorbic acid 2-phosphate magnesium | — | — | — | — | 0.5 | — |
| Distilled water | to 100 | to 100 | to 100 | to 100 | to 100 | to 100 |

EXAMPLE 2 AND COMPARATIVE EXAMPLES 6~10 SKIN SOFTNERS

M

|  | Example | Comparative Examples | | | | |
|---|---|---|---|---|---|---|
| Materials | 2 | 6 | 7 | 8 | 9 | 10 |
| Distilled water | to 100 | to 100 | to 100 | to 100 | to 100 | to 100 |
| POE-16 octyldodecylether | 0.5 | 0.5 | 0.5 | 0.5 | 0.5 | 0.5 |
| Polysorbate-60 | 0.5 | 0.5 | 0.5 | 0.5 | 0.5 | 0.5 |
| Glycerine | 10.0 | 10.0 | 10.0 | 10.0 | 10.0 | 10.0 |
| Propyleneglycol | 9.0 | 9.0 | 9.0 | 9.0 | 9.0 | 9.0 |
| Polyethylene glycol 4000 | 3.0 | 3.0 | 3.0 | 3.0 | 3.0 | 3.0 |
| Alantoin | 0.3 | 0.3 | 0.3 | 0.3 | 0.3 | 0.3 |
| Sodium carboxymethylcellulose | 0.2 | 0.2 | 0.2 | 0.2 | 0.2 | 0.2 |
| L-ascorbic acid(AsA) | — | — | 0.5 | — | — | 0.25 |
| 3-Aminopropane phosphoric acid(3-APPA) | — | — | — | 0.5 | — | 0.25 |
| AsA-APPA(Prep. Ex. 3) | 0.5 | — | — | — | — | — |
| L-ascorbic acid 2-phosphate magnesium | — | — | — | — | 0.5 | — |
| Ethanol | 7.0 | 7.0 | 7.0 | 7.0 | 7.0 | 7.0 |
| Perfume | q.s. | q.s. | q.s. | q.s. | q.s. | q.s. |
| Preservative | q.s. | q.s. | q.s. | q.s. | q.s. | q.s. |

13

-continued

| <Evaluation System> |
|---|
| – No irritation, estimated to be adequate for the sensitive skin |
| = No irritation in repeat application |

TABLE 6

| | Examples | | Comparative Examples | | | | | | | | | |
|---|---|---|---|---|---|---|---|---|---|---|---|---|
| | 1 | 2 | 1 | 2 | 3 | 4 | 5 | 6 | 7 | 8 | 9 | 10 |
| Evaluation | = | – | = | – | = | ± | ± | = | + | ± | ± | – |

As shown in Table 6, the compositions containing AsA-APPA is no irritative to the skin.

EXPERIMENTAL EXAMPLE 6 WHITENING EFFECT

In order to evaluate skin-whitening effect of cosmetic compositions containing AsA-APPA, the following experiment was carried out for compositions of Examples 1~2 and Comparative Examples 1~10.

To lower parts of both the arms of ten(10) healthy volunteers were applied patch having four(4) holes of 1.5 cm diameter and were irradiated with an UV-ray using TL20W/12UV lamp(Philips) and TL20W/09UV lamp(Philips) at a distance of 10 cm therefrom at 1.5 MED once a day for 2 days. Then, the subjected were divided into two groups, A and B. To A group was applied each of the creams prepared in Example 1 and Comparative Examples 1~5 and to B group was applied each of the skin softeners prepared in Example 2 and Comparative Examples 6~10 two times a day for 6 weeks. The skin-whitening effect was observed with naked eyes and evaluated: No effect, Effective, and Significant effect. The results are shown in Table 7.

TABLE 7

| Sample Composition | Significant effect | Effective | No effect |
|---|---|---|---|
| Example 1 | 2 | 2 | 6 |
| Example 2 | 1 | 3 | 6 |
| Comparative Example 1 | — | — | 10 |
| Comparative Example 2 | 3 | 1 | 6 |
| Comparative Example 3 | — | 1 | 9 |
| Comparative Example 4 | 1 | 3 | 6 |
| Comparative Example 5 | 1 | 2 | 7 |
| Comparative Example 6 | — | — | 10 |
| Comparative Example 7 | 1 | 2 | 7 |
| Comparative Example 8 | — | 1 | 9 |
| Comparative Example 9 | 1 | 1 | 8 |
| Comparative Example 10 | — | 1 | 9 |

As shown in Table 7, the whitening effect of the composition containing AsA-APPA(Ex. 1 or 2) is similar to that of the composition containing L-ascorbic acid 2-phosphate magnesium(C. Ex. 4 or 9), while it is slightly less than that of the composition containing AsA(C. Ex. 2 or 7).

What is claimed is:

1. 2-(3-aminopropane phosphoric acid)-L-ascorbate represented by a following general formula (I) or its salt:

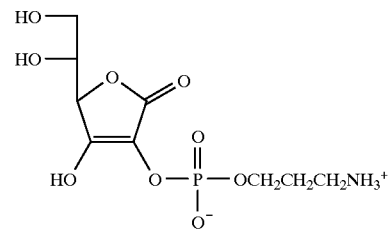

2. The 2-(3-Aminopropane phosphoric acid)-L-ascorbic compound according to claim 1, wherein said salt is selected from the group consisting of salts by alkaline metals selected from the group consisting of sodium and potassium, salts by alkaline earth metals selected from the group consisting of calcium and magnesium; salts by basic amino acids selected from the group consisting of lysine, arginine and histidine; salts by ammonia and amides selected from the group consisting of triethanol amine; salts by cationic polymers selected from the group consisting of polyquaternium-4, -6, -7, -10, -11, and -16; and salts by cationic surfactants selected from the group consisting of lauryldimethylbenzyl ammonium chloride and stearyldimethylbenzyl ammonium chloride.

3. A method for preparing said 2-(3-Aminopropane phosphoric acid)-L-ascorbate of claim 1, which comprises steps of:

(1) reacting 3-amino-1-propanol with phosphorus oxychloride in an equivalent ratio of 1:1~1.3, in presence of an organic base, in an organic solvent, at a temperature of 0~5° C. for 1~2 hours, to produce 2-chlorotetrahydro-2H-1,3,2-oxazaphosphorin P-oxide represented by a following general formula (II):

(2) reacting said compound (II) of said step (1) with 5,6-hydroxyl groups-protected L-ascorbic acid, in presence of an organic base, in an organic solvent, to produce L-ascorbic acid derivative represented by a following general formula (III):

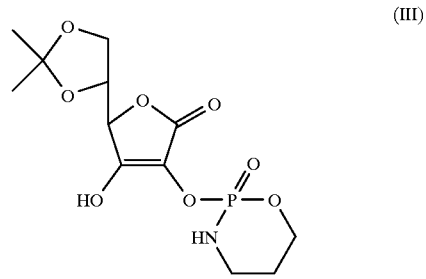

(3) hydrolyzing the L-ascorbic acid derivative (III) of said step (2) by adding distilled water thereto, at a temperature of 5~100° C. for about 3 hours, to produce 2-(3-aminopropane phosphoric acid)-L-ascorbate;

(4) recrystallizing the product of said step (3) with a polar organic solvent; and (5) optionally neutralizing the product of said step (4) with an alkali or a base, to form a salt.

4. The method according to claim 3, wherein said organic base of said step (1) is pyridine or triethylamine.

5. The method according to claim 3, wherein said organic solvent of said step (1) is selected from a group consisting of dichloromethane, tetrahydrofuran, ethyl acetate, acetonitrile, chloroform, ethyl ether and other inert solvents.

6. The method according to claim 3, wherein a protecting group employed in masking 5,6-hydroxyl groups of L-ascorbic acid is selected from a group consisting of benzylidene, phenylethylidene and isopropylidene.

7. The method according to claim 3, wherein said organic base of said step (2) is pyridine or triethylamine.

8. The method according to claim 3, wherein said organic solvent of said step (2) is selected from a group consisting of dichloromethane, tetrahydrofuran, ethyl acetate, acetonitrile, chloroform, ethyl ether and other inert solvents.

9. The method according to claim 3, wherein a salt is formed.

10. The method according to claim 9, wherein a neutralizing agent is employed in said step (5) and is selected from the group consisting of alkali, metal oxides selected from the group consisting of sodium carbonate, sodium hydroxide, potassium carbonate, potassium hydroxide, calcium hydroxide, magnesium hydroxide, calcium oxide, and magnesium oxide; basic amino acids selected from the group consisting of lysine, arginine and histidine; ammonia or amides such as selected from the group consisting of triethanol amine; cationic polymers selected from the group consisting of polyquaternium-4, -6, -7, -10, -11, and -16; and cationic surfactants selected from the group consisting of lauryldimethylbenzyl ammonium chloride and stearyldimethylbenzyl ammonium chloride.

11. A skin-whitening cosmetic composition containing said 2-(3-Aminopropane phosphoric acid)-L-ascorbate or its salt of claim 1.

12. The skin-whitening cosmetic composition according to claim 11, which contains said 2-(3-Aminopropane phosphoric acid)-L-ascorbate or its salt in an amount of 0.005~10% by weight.

* * * * *